United States Patent [19]
Duve et al.

[11] Patent Number: 5,863,763
[45] Date of Patent: Jan. 26, 1999

[54] INSECT NEUROPEPTIDES

[75] Inventors: Hanne Duve; Alan Thorpe, both of London, England; Anders Holten Johnsen, Copenhagen, Denmark

[73] Assignee: British Technology Group Ltd., London, England

[21] Appl. No.: 714,053

[22] PCT Filed: Mar. 9, 1995

[86] PCT No.: PCT/GB95/00505

§ 371 Date: Sep. 11, 1996

§ 102(e) Date: Sep. 11, 1996

[87] PCT Pub. No.: WO95/24423

PCT Pub. Date: Sep. 14, 1995

[30] Foreign Application Priority Data

Mar. 9, 1994 [GB] United Kingdom ............... 9404529

[51] Int. Cl.⁶ .................. C12D 21/06; A61K 38/04; A61K 38/00; C07K 5/00
[52] U.S. Cl. ................ 435/69.1; 530/328; 530/329; 530/333; 514/15; 514/16
[58] Field of Search .................. 530/328, 333, 530/329; 435/69.1; 514/15, 16

[56] References Cited

FOREIGN PATENT DOCUMENTS

WO 97/38121  10/1997  WIPO .

OTHER PUBLICATIONS

Bellés, X., et al., "In Vivo and in Vitro Effects of Compactin in Liposome Carriers on Juvenile Hormone Biosynthesis in Adult Females of *Blattella germanica*," *Pesticide Biochem. Physiol.* 32:1–10 (1988).

Duve, H., et al., "Callatostatins: Neuropeptides from the blowfly *Calliphora vomitoria* with sequence homology to cockroach allatostatins," *Proc. Natl. Acad. Sci. USA* 90(6):2456–2460 (Mar. 15, 1993).

Duve, H., and Thorpe, A., "Distribution and funtional significance of Leu–callatostatins in the blowfly *Calliphora vomitoria*" *Cell Tissue Res.* 276(2):367–379 (May 1994).

Duve, H., et al., "[Hyp³]Met–callatostatin," *J. Biol. Chem.* 269(33):21059–21066 (Aug. 19, 1994).

Kramer, S.J., et al., "Identification of an allatostatin from the tobacco hornworm *Manduca sexta*," *Proc. Natl. Acad. Sci. USA* 88:9458–9462 (1991).

Piulachs, M.D., et al., "Juvenile Hormone Production and Accessory Reproductive Gland Development During Sexual Maturation of Male *Blattella germanica* (L.) (Dictyoptera, Blattellidae)," *Comp. Biochem. Physiol.* 102A(3):477–480 (1992).

Pratt, G.E., et al., "Identity of a second type of allatostatin from cockroach brains: An octadecapeptide amide with a tyrosine–rich address sequence," *Proc. Natl. Acad. Sci. USA* 88:2412–2416 (1991).

Vuori, K., et al., "Characterization of the human prolyl 4–hydroxylase tetramer and its multifunctional protein disulfide–isomerase subunit synthesized in a baculovirus expression system," *Proc. Natl. Acad. Sci. USA* 89:7467–7470 (1992).

Vuori, K., et al., "Site–directed mutagenesis of human protein disulphide isomerase: effect on the assembly, activity, and endoplasmic reticulum retention of human prolyl 4–hydroxylase in *Spodoptera frugiperda* insect cells," *EMBO J.* 11:4213–4217 (1992).

Weaver, R.J., "Profile of the Responsiveness of Corpora Allata from Virgin Female *Periplaneta americana* to an Allatostatin from *Diploptera punctata*," *J. Insect Physiol.* 37:111–118 (1991).

Woodhead, A.P., et al., "Primary structure of four allatostatins: Neuropeptide inhibitors of juvenile hormone synthesis," *Proc. Natl. Acad. Sci. USA* 86:5997–6001 (1989).

*Primary Examiner*—Paula K. Hutzell
*Assistant Examiner*—Mark Navarro
*Attorney, Agent, or Firm*—Nixon & Vanderhye

[57] ABSTRACT

The present invention relates to novel peptides isolated from the blowfly *Calliphora vomitoria*. The invention also relates to nucleic acid molecules encoding these peptides, vectors and host cells comprising these nucleic acid molecules, and chemical and biological methods for producing these peptides. The present peptides have novel sequences comprising hydroxyproline residues and C-terminal amide groups which give the peptides improved stability in the gut of insects. The peptides of the invention are related to the allatostatin class of insect neuropeptides, have inhibitory effects on gut motility in the blowfly *C. vomitoria*, and have allatostatic effects in cockroaches of the species *Diploptera punctata* and *Periplaneta americana*. The invention also provides compositions comprising the present peptides which may be used as insecticides, and provides methods of killing or controlling insects comprising administering the nucleic acid molecules, peptides or compositions of the invention to insects.

15 Claims, 2 Drawing Sheets

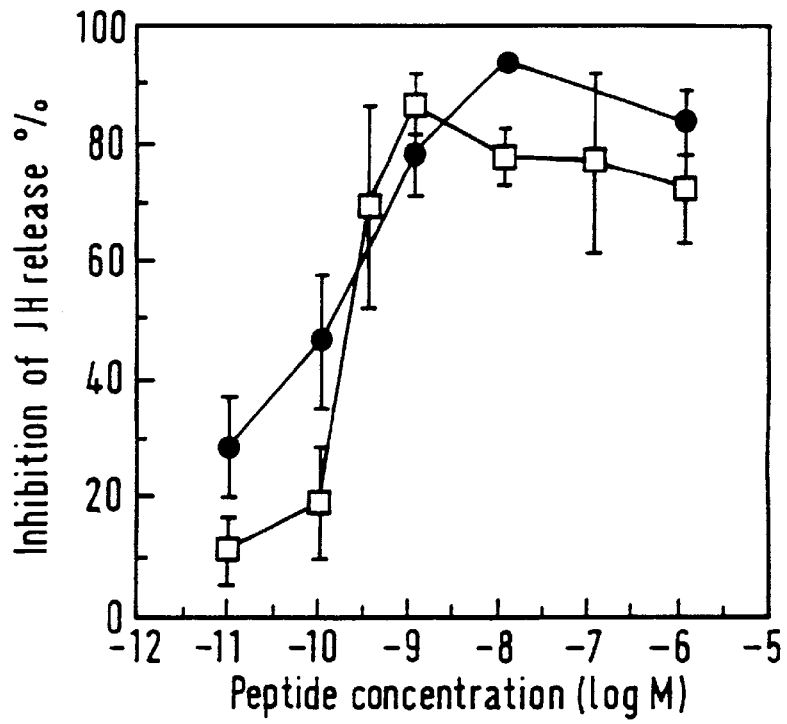
FIG. 1.  ● Met-cast   ☐ [Hyp3] Met-cast
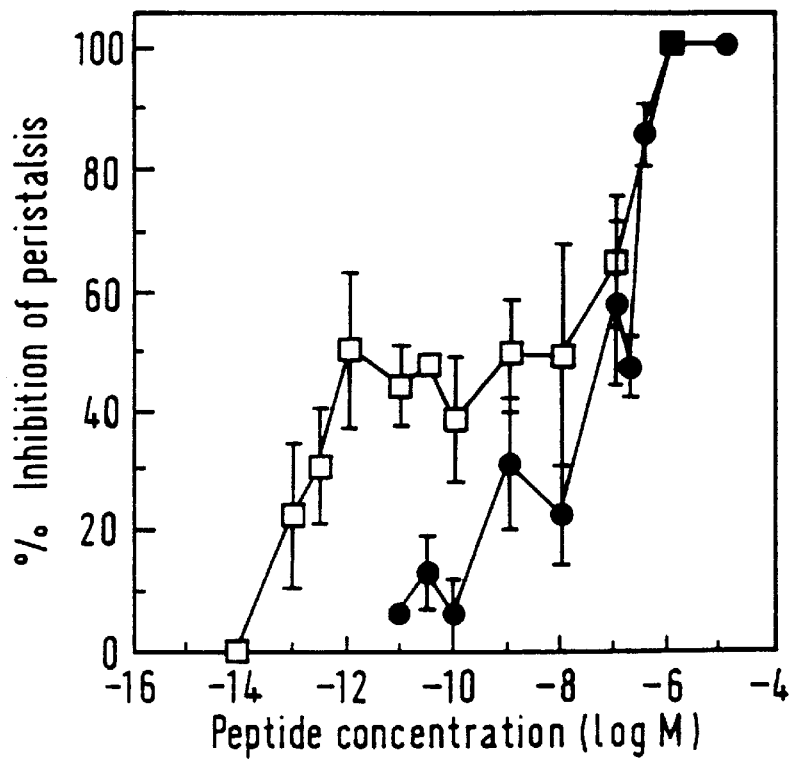
FIG. 2.  ● Met-cast   ☐ [Hyp3] Met-cast

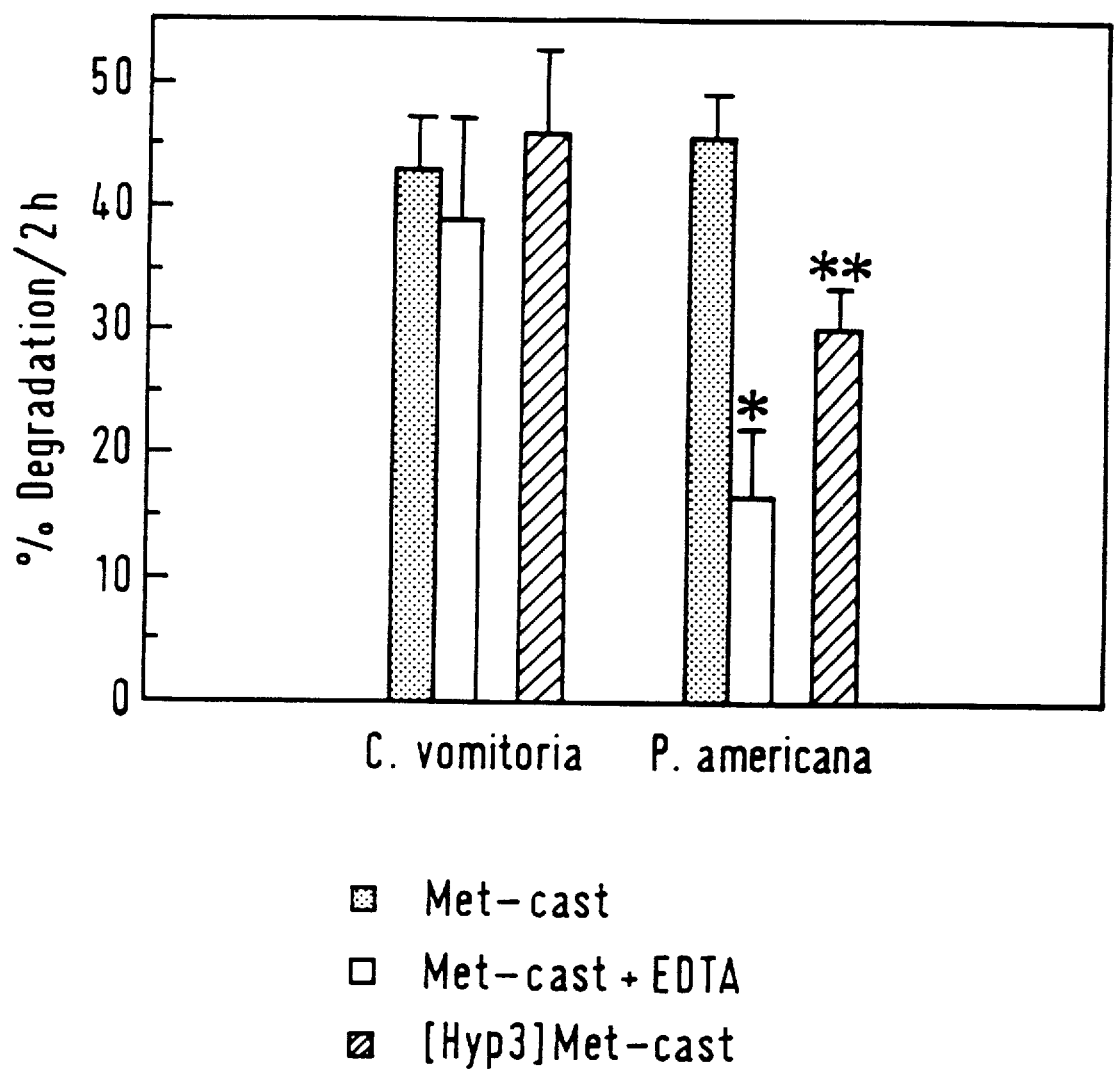

INSECT NEUROPEPTIDES

FIELD OF THE INVENTION

The present invention relates to novel neuropeptides isolated and purified from the blowfly *Calliphora vomitoria*, which have been designated callatostatins. This new class of neuropeptides may be related to the allatostatin class of neuropeptides isolated from other unrelated insect species.

BACKGROUND OF THE INVENTION

The first group of callatostatins to be isolated from *Calliphora vomitoria*, callatostatins 1 to 5, were shown to have some sequence homology to cockroach allatostatins (Duve et al in *Proc. Nat'l. Acad, Sci.* USA 90:2456–2460). The neuropeptides have the following sequences 1. Asp-Pro-Leu-Asn-Glu-Glu-Arg-Arg-Ala-Asn-Arg-Tyr-Gly-Phe-Gly-Leu-NH$_2$ (SEQ ID NO:4)
2. Leu-Asn-Glu-Glu-Arg-Arg-Ala-Asn-Arg-Tyr-Gly-Phe-Gly-Leu-NH$_2$ (SEQ ID NO:5)
3. Ala-Asn-Arg-Tyr-Gly-Phe-Gly-Leu-NH$_2$ (SEQ ID NO:6)
4. Asp or Asn-Arg-Pro-Tyr-Ser-Phe-Gly-Leu-NH$_2$ (SEQ ID NO:7)
5. Gly-Pro-Pro-Tyr-Asp-Phe-Gly-Met-NH$_2$ (SEQ ID NO:8)

Callatostatins 1 to 4 (SEQ ID NOS:4–7) are know as Leu-callatostatins and callatostatin 5 (SEQ ID NO:8) is known as Met-callatostatin or Met-cast.

The allatostatin class of insect neuropeptides in cockroaches have been shown capable of inhibiting the production of juvenile hormone (JH) by the corpus allatum. The corpus allatum (CA) is a classical endocrine gland of insects situated in close proximity to the brain with which it has nervous connection. To date, members of the allatostatin class of neuropeptides have been isolated and identified in only four species, from three different orders of insects. In the cockroach, *Diploptera punctata* (Order: Blattodea) five allatostatins ranging in size from 8 to 18 amino acids have been characterized (Pratt et al in *Proc. Nat'l. Acad. Sci* USA 88, 2412–2416 (1991) and Woodhead et al in *Proc. Nat'l. Acad. Sci.* USA 86, 5997–6001 (1989)). Two other allatostatins have also been identified in the cockroach *Periplaneta americana* (Order: Blattodea) (Weaver et al in *C Comp. Pharmacol. Toxicol.* 107 119–127 (1994)) and in the tobacco hornworm moth. *Manduca sexta* (Order: Lepidoptera) a further allatostatin has been identified (Kramer et al in *Proc. Nat'l. Acad. Sci.* USA 88, 9458–9462 (1991)).

The significance of the allatostatins—(and callatostatins) lies in the fact that "in vitro" they have been shown, with the exception of the allatostatin from the tobacco hornworm moth, to inhibit the production of juvenile hormone (JH) by the corpus allatum in cockroaches. The allatostatin molecule isolated from the tobacco hornworm moth inhibits JH production in the species in which it is found i.e. *Mandus sexta* but not in cockroaches. Callatostatins 1 to 5 (SEQ ID NOS:4–8) are of interest because they are potent inhibitors of JH synthesis and release in cockroaches, but not in the blowfly, the species from which they originate.

Juvenile hormone plays a crucial role in insect development by controlling metamorphosis, adult sexual maturity and reproduction. Interference with juvenile hormone biosynthesis and release through exploitation of the allatostatins and callatostatins may lead to insect control strategies that do not damage the environment.

SUMMARY OF THE INVENTION

The present invention is based on the discovery and potential practical commercial application of one or more of three neuropeptides identified in the blowfly *Calliphora vomitoria*. The three peptides are all related to callatostatin 5 (SEQ ID NO:8) and might even be derived from the same prohormone by post-translation modification.

DETAILED DESCRIPTION OF THE PREFERRED EMBODIMENTS

The amino acid sequences of the neuropeptides according to this invention are as follows:

1. Gly-Hyp-Pro-Tyr-Asp-Phe-Gly-Met-NH$_2$ (SEQ ID NO:1) (designated [Hyp$^2$]Met-callatostatin or [Hyp$^2$] Met-cast)
2. Gly-Pro-Hyp-Tyr-Asp-Phe-Gly-Met-NH$_2$ (SEQ ID NO:2) (designated [Hyp$^3$]Met-callatostatin or [Hyp$^3$] Met-cast)
3. Pro-Tyr-Asp-Phe-Gly-Met-NH$_2$ (SEQ ID NO:3) (designated Met-callatostatin 3–8 or des-Gly-Pro-Met-callatostatin).

The invention embraces neuropeptides 1–3 defined above when isolated and/or when substantially purified and essentially free of other peptide material.

The presence of the hydroxyproline residues (Hyp) has been confirmed by amino acid analysis and confirmation that the final methionyl residue of peptide No. 1 (SEQ ID NO:1) above is carboxyamidated was obtained by means of standard methylation procedures and comparisons of the masses of methylated and non-methylated peptides. The carboxyamidation of peptides 2 (SEQ ID NO:2) and 3 (SEQ ID NO:3) above is shown by the fact that they are both immunoreactive in the met-callatostatin radioimmunoassay. This recognizes only amidated peptides.

The invention also embraces insecticidal compositions which contain one or more the above neuropeptides 1–3 described above, which may be a liposomal formulation, and methods of killing or controlling insects which involve applying to the insects or their environment such insecticidal compositions. The insecticidal compositions may contain besides at least one insecticidally effective neuropeptide 1–3 described above, a suitable carrier, diluent or excipient therefor. The formulations according to the present invention may be administered in the form of a spray.

Methods of making insecticidal compositions are also embraced by the present invention which comprises admixing one or more the said neuropeptides 1–3 above with a suitable carrier, diluent or excipient therefor.

The neuropeptides 1–3 described above can be synthesized by the skilled worker by routine peptide synthesis by selecting the appropriate amino acids and reaction conditions.

The use of such peptides as an insecticide is also within the scope of the present invention which may comprise the inhibition of gut motility. The use of such insecticidal compositions may be specific for the codling moth *Cydia pomonella*.

The invention also extends to vector systems comprising a DNA sequence which encodes a neuropeptide as described above and a prolylhydroxylase enzyme for expression in the same cell. Vector systems include single vectors expressing both the neuropeptide and the prolyl hydroxylase and pairs of vectors, wherein one vector of the pair expresses the the neuropeptide and the other expresses the prolyl hydroxylase. Suitable vectors are preferably specific for the target organism and may be baculovirus based.

The neuropeptides described by the present invention are only the second group of the allatostatin class of compounds to be isolated from this major order of insects, the Diptera. The first was also from this species, the blowfly *Calliphora vomitoria*.

The callatostatin peptides differ from all the other known allatostatins of cockroaches (Order: Blattodea) in that the C-terminal residue is Met-$NH_2$ and not Leu-$NH_2$ or Ile-$NH_2$. The callatostatin peptides previously isolated from the blowfly Calliphora vomitoria were not shown to have any hydroxyproline amino acid residues in their sequences.

The occurrence of the hydroxyproline residue (presumably by post-translational modification of the proline residue) is extremely rare in bioactive peptides. In mammals, only a very few bioactive peptides are known to contain a hydroxyproline residue and they include the luteinizing hormone-release hormone (LH-RH) and bradykinin. In insects only one other instance of a hydroxylated proline residue has been reported so far, in a protein of the mosquito Aedes egypti, designated Aea HP-I.

It is thought to be unique for both the first and the second proline residues in a Gly-Pro-Pro sequence to be shown capable of hydroxylation. In the protein collagen, where hydroxylation is a common occurrence, the sequence Gly-Pro-Pro occurs several times and it is unknown for the first proline to be hydroxylated. This suggests that a fundamentally different prolyl hydroxylase enzyme substrate specificity is operating in the tissues of Calliphora vomitoria.

The combination of the C-terminal Met-$NH_2$ and the N-terminal Gly-Hyp-Pro or Gly-Pro-Hyp sequence appears to make the callatostatin peptides extremely difficult to degrade. Experiments have shown that enzymes in the haemolymph of cockroaches are able to degrade Cast-5 (SEQ ID NO:8) (Gly-Pro-Pro) but not the two peptides with the Gly-Hyp-Pro (SEQ ID NO:1) or Gly-Pro-Hyp (SEQ ID NO:2) motifs. Hydroxylation of the proline residues may therefore confer a conformational stability to the molecules which protects them against enzymatic degradation.

Several of the properties of the peptides described by the present invention make the peptides potentially important as non-chemical insecticidal agents. Firstly, their bioactivity as active inhibitors of muscular contraction of the gut (and also possibly the heart) and their ability to affect JH biosynthesis, as least in cockroaches. Secondly, the presence of the hydroxylated proline residue(s) appears to make the peptides very resistant to degradation, a fact which greatly increases their potency. Thirdly, the substitution of the methionyl residue for the leucyl residue at the C-terminus also appears to render the peptides less susceptible to degradation, particularly if implanted into a "foreign" host i.e. a non-dipteran species.

The peptides therefore appear to have general application as insecticides effective against dipteran and non-dipteran species. Suitable target organisms include the noctuid moths and in particular the codling moth Cydia pomonella.

One route for the administration of the peptides for use as an insecticide could be to encapsulate the peptides in a liposomal formulation (Belles et al in Pesticide Biochem. Physiol. 32, 1–10 (1988)).

Another mechanism by which the peptides could be inserted in large quantity into pest species such as the codling moth is through a baculovirus that is specific for the pest species and for no other species. Such a process involves inserting a length of DNA constructed from knowledge of the peptide amino acid sequence, or by isolation of the specific gene from Calliphora vomitoria, into the baculovirus thus causing it to express large quantities into the host insect species. The baculovirus could also be engineered to co-express a gene encoding a prolylhydroxylase enzyme. The enzyme prolyl 4-hydroxylase has been characterised and expressed in a baculovirus system (Vuori et al in EMBO J. 11, 4213–4217 (1992) and Vuori et al in Proc. Nat'l. Acad. Sci. 89, 7467–7470 (1992)).

This model applies to any insect pest species capable of being infected by a specific baculovirus and which is also physiologically damaged by the presence of peptide expressed at high levels into the haemolymph. The peptides that are the subject of the present invention appear to be ideally suited for exploitation in this way and their value as non-toxic, environmentally-friendly insecticidal agents could be considerable.

BRIEF DESCRIPTION OF THE FIGURES

The invention will now be described by way of example with reference to the accompanying Examples which are provided for the purposes of illustration and are not to be construed as being limiting on the present invention. Reference is made in the Examples to a number of figures in which:

FIG. 1 shows the dose response for inhibition of Juvenile Hormone III release from corpora allata of virgin P. americana by Met-callatostatin (SEQ ID NO:8) and [Hyp$^3$]Met-callatostatin (SEQ ID NO:2).

FIG. 2 shows the dose responses for inhibition of peristalsis of the hindgut of C. vomitoria by Met-callatostatin SEQ ID NO:8 and [Hyp$^3$]Met-callatostatin (SEQ ID NO:2).

FIG. 3 shows the degradation of Met-callatostatin (SEQ ID NO:8) and [Hyp$^3$]Met-callatostatin (SEQ ID NO:2) by haemolymph of C. vomitoria and P. americana.

EXAMPLES

Example 1: Isolation and purification of peptides

The peptides were isolated from extracts of the heads (approximately 12000) of the blowfly Calliphora vomitoria according to the following procedure.

Approximately 12,000 heads from C. vomitoria, 1–3 weeks old and fed a diet of sugar, Ovaltine, and water, were collected by freezing flies with solid $CO_2$, shaking them in a plastic bag, and sieving the separated parts. After grinding in solid $CO_2$, the heads were extracted in batches of 2000 in a mixture of 400 ml of methanol/glacial acetic acid/water (87:5:8) at 22° C. The extract was ultrasonicated for 2 min and centrifuged at 3000×g for 5 min after which the supernatant was filtered through Whatman™ No. 4 paper. The pellet was re-extracted with 2×100 ml of extraction fluid, and the filtered supernatants were combined and concentrated to 100 ml on a rotary evaporator at 35° C. under vacuum. The concentrate was centrifuged at 3000×g at 4° C. for 10 min, and the supernatant was collected. To 100 ml of concentrate was added 400 ml of acetone, and, after stirring, the mixture was kept at 22° C. overnight. The clear liquid was decanted from the precipitate and concentrated almost to dryness before being taken up into the start solvent for HPLC (5% acetonitrile, 0.1% trifluoroacetic acid). The acetone precipitate was dissolved in 64 ml of the start solvent and stored at 4° C. prior to HPLC.

The HPLC steps were as follows:
(i) Waters™ $C_{18}$, 300×7.8 mm, 10 μm, 125 Å, $CH_3CN$/0.1% TFA, 1.3%/min, 1.5 ml/min.
(ii) Waters™ $C_{18}$, 300×7.8 mm, 10 μm, 125 Å, $CH_3CN$/10 mM $NH_4OAc$, pH 6.5, 0.5%/min, 1.5 ml/min.
(iii) BioRad Hi-Pore™ $C_4$, 250×4.6 mm, 5 μm, 300 Å $CH_3CN$/0.1% TFA, 0.5%/min, 1.5 ml/min.
(iv) Kromasil™ $C_{18}$, 250×4.6 mm, 5 μm, 300 Å, $CH_3CN$/0.1% TFA, 0.3%/min, 1 ml/min
(v) Vydac™ $C_{18}$, 150×1.2 mm, 5 μm, 300 Å, $CH_3CN$/0.1% TFA, 0.5%/min, 0.2 ml/min.

Both precipitate and supernatant yielded members of the callatostatin neuropeptide family. To avoid loss or damage to the peptides, immunoreactive fractions at all stages were not lyophilized but were diluted to give a 5–10% $CH_3CN$ concentration and were pumped directly onto the HPLC column.

Example 2: Amino acid analysis

The purified peptides (50–100 pmol) were hydrolysed for 20 h in 6M HCl gas phase at 110° C. under argon in pyrolysed microvials (100 μl, Hewlett-Packard). The hydrolysate was dried and redissolved in 8 μl of 0.4M sodium borate, pH 10.4. Amino acid analysis was performed on 6 μl after precolumn derivatisation with phthalaldehyde followed by 9-fluorenylmethyl chloroformate using a Hewlett-Packard Aminoquant™ analyzer. For calibration, hydroxyproline was included in the standard mixture of the common 16 amino acids obtained by acid hydrolysis (Sigma).

Example 3: Amino acid sequence analysis

The amino acid sequences of the purified peptides (5–50 pmol) were determined with an automated protein sequencer (Applied Biosystems 475A) equipped with an on-line system for the detection of the amino acid phenylthiohydantoin derivatives, which were separated on a $C_{18}$-DB column (5-7943, Supelco).

Example 4: Mass Spectrometry

A portion (5–50 pmol) of the purified peptides was analysed by using a Bio-Ion™ 20 plasma desorption time-of-flight mass spectrometer (Applied Biosystems). The dried samples were dissolved in 10 μl of 0.1% trifluoroacetic acid in 20% $CH_3CN$, and two 5-μl aliquots were applied to aluminized Mylar™ foil (coated with nitrocellulose) and evaporated. The spectra were recorded for $1–6 \times 10^6$ primary ions. The method has an accuracy of 0.1%. The possible amidation of the carboxy-terminus was assessed by determining the total number of free carboxyl groups by methylation of an aliquot and remeasurement of the molecular mass (Talbo et al in *Eur. J. Biochem.* 195, 495–504 (1991)).

Example 5: Generation of antisera

Met-callatostatin carboxy-terminal-specific antisera for radioimmunoassay (RIA) and immunocytochemistry (ICC) were generated in Dutch rabbits as previously described (Duve et al in *Cell Tissue Res.* 276 367–379 (1994)). Met-callatostatin was synthesised with the $NH_2$-terminal addition of Cys-βAla-βAla and conjugated to keyhole limpet haemocyanin using 3-maleimido-benzoic acid N-hydroxysuccinimide ester (synthesis and conjugation carried out by Affinity Research Products Ltd, Nottingham, United Kingdom).

Example 6: Radioimmunoassay for Met-callatostatin

A Radioimmunoassay (RIA) specific for Met-callatostatin was developed to monitor fractions during the purification. Met-callatostatin was iodinated with $^{125}I$ using chloramine T in the presence of phosphate buffer, pH 7.4, for 30 s. The iodinated peptide was eluted from a $C_{18}$ Sep-Pak™ (Waters) with 1 ml of methanol, 0.1% trifluoroacetic acid. For assay, samples were dried and resuspended in 200 μl of 50 mM phosphate buffer, pH 7.4. Aliquots of antiserum (Rabbit D1 Bleed 4), 1:3000, 50 μl) and $^{125}I$-Met-callatostatin (10,000 cpm, 50 μl) were added, and the mixture was incubated for 20 h at 4° C. Antibody-bound and free tracer were then separated as previously described (Duve et al in *Regul. Pept.* 35 145–159 (1991)). The RIA provided specific for carboxy-terminally amidated Met-callatostatin (SEQ ID NO:8). Thus, the Leu-callatostatins (SEQ ID NOS:4–7) were recognised only at the 0.01% level, while the synthetic free acid analogue of Met-callatostatin was not recognised at the 0.01% level.

Example 7: Allostatic activity of [Hyp$^3$]Met-callatostatin

The peptide [Hyp$^3$]Met-callatostatin (SEQ ID NO:2) was tested for its allostatic activity in the blowfly *C. vomitoria* and in cockroaches of the species *P. americana* and *B. germanica*.

Radiochemical Assays to Determine Allatostatic Activity

Peptides identified from the extracts were synthesized (Affinity Research Products) and tested in radiochemical assays to determine their effects on the synthesis and release of juvenile hormone bisepoxide from the isolated CA of vitellogenic female *C. vomitoria*. Similar assays were also carried out on the CA of the cockroaches *P. americana* (4- to 6-day-old virgin females) and *B. germanica* (6-day-old virgin females). Details of the methods used have been published previously (*C. vomitoria* in Duve et al in *Proc. Nat'l. Acad. Sci.* USA 90 2456–2460 (1993), *P. americana* in Weaver et al in *C Comp. Pharmacol. Toxicol.* 107, 119–127 (1994), and Weaver, R. C. in *J. Insect Physiol.* 37, 111–118 (1991), and *B. germanica* in Piulachs et al in *A Comp. Physiol.* 102, 477–480 (1992). For *C. vomitoria* and *P. americana* the donor methyl group for incorporation into the JH was provided by L-[methyl-$^{14}$C]methionine, 2.04 GBq/mmol (Amersham International plc), added to methionine-free TCC 199 medium to give a final concentration of 260 μM and for *B. germanica* by L-[methyl-$^3$H] methionine, 3.03 TBq/mmol (Amersham) added to TCC 199 medium containing methionine to achieve a concentration of 100 μM and a final specific activity of 7.4 GBq/mmol.

For comparison, the activity of Met-callatostatin was also assayed. FIG. 1 shows the dose responses for the inhibition of JH III release from corpora allata of virgin (4- to 6-day-old) *P. americana* by Met-callatostatin (SEQ ID NO:8) and [Hyp$^3$]Met-callatostatin (SEQ ID NO:2). The results of the experiment in FIG. 1 shows the percentage inhibition of groups of treated glands (one-half of a group six to seven glands) relative to untreated groups (the corresponding half of the pairs of glands) for three hour incubations. Vertical error bars show the standard error of the mean (callatostatin is abbreviated to cast in the figure).

Both the Met- and [Hyp$^3$]Met-callatostatin peptides (SEQ ID NOS: 8 and 2, respectively) inhibited JH release from the isolated CA of the cockroach *P. americana* as shown in FIG. 1. There was no significant difference in the potencies of the two peptides ($IC_{50}$=0.1 nm). They also proved equipotent in *B. germanica*, although a higher concentration ($IC_{50}$=1 μm) was required (results not shown). In contrast neither peptide had any effect on the release of juvenile hormone bisepoxide from the CA of *C. vomitoria* results not shown).

The three neuropeptides are active inhibitors of juvenile hormone (JH) production in the two cockroaches *Periplaneta americana* and *Blattella germanica*. Maximum inhibition occurring at between $10^{-8}$ and $10^{-6}$M.

Example 8: Effect of the peptides in the hindgut of blowfly

The effects of both the Met- and [Hyp$^3$]Met-callatostatin peptides (SEQ ID NOS:8 and 2, respectively) on the motility of the hindgut of *C. vomitoria* were investigated.

Adult female *C. vomitoria* were fed sugar, water and meat for 7 days prior to studying the effect of synthetic peptides (Affinity Research Products Ltd, Nottingham) on gut motility. The stage of development of the oocytes of each fly was recorded to provide a physiological base line. The gut and reproductive system were transferred to a 100-μl Sylgard chamber (Sylgard 184, Dow Corning) and bathed in a Calliphora Ringer's solution (Duve et al in *Regul. Pept.* 35 145–159 (1991)). Peristaltic movements of the ileum and the other forms of contraction in the rest of the gut and reproductive musculature were observed under a microscope. The preparation was superfused with several washes of Ringer's solution, after which peristaltic movements of the ileum were counted over a 2-minute period. The bathing fluid was replaced with fresh Ringer's solution containing the test peptide and the counting repeated. This procedure could be carried out many times for a single preparation.

Peptide solutions were made up in Ringer's solution on the day of the experiments, which were carried out at 22° C. Approximately 50 female flies were used.

The normal peristaltic movements (9–10/min) of the ileum of C. vomitoria were completely inhibited by both variants of Met-callatostatin at 1 μm and the results of the experiments are shown in FIG. 2. FIG. 2 shows the dose responses for inhibition of peristalsis of the hindgut of C. vomitoria by Met-callatostatin and [Hyp$^3$]Met-callatostatin displayed as the percentage inhibition relative to basal spontaneous peristaltic movements. Each point represents the mean of 5–16 measurements from a number of different vitellogenic female flies (callatostatin is abbreviated to cast in the figure). However, whereas Met-callatostain shows a monophasic dose-response curve with an IC$_{50}$ of 100 nm, [Hyp$^3$]Met-callatostatin has a biphasic dose-response curve with IC$_{50}$ values of 0.5 pm and 0.5 μm.

As described in connection with Example 7, in experiments on the adult blowfly, the peptides do not appear to act in the control of juvenile hormone synthesis and/or release. However, they do act as potent inhibitors of the peristaltic contraction of the gut at concentration between $10^{-16}$ to $10^{-9}$M. Axons containing these peptides also pass to the heart and it is probable that they have a regulatory role on the activity of this organ.

Example 9: Biostability of the peptides in P. americana and C. vomitoria

Degradation of the both Met- and [Hyp$^3$]Met-callatostatin peptides (SEQ ID NOS: 8 and 2, respectively) was investigated in P. americana and C. vomitoria.

Degradation of the Met-callatostatins induced by the haemolymph was assessed by measuring the difference between the amount of added peptide at the start of the incubation period and the total immunoassayable material present at its conclusion. Since the radioimmunoassay (RIA) is carboxy-terminal specific, any degradation at the carboxy-terminus, as for example by metalloendopeptidases able to cleave the Phe-Gly bond (Lamango et al in *Insect Biochem. Mol. Biol.* 23, 801–808 (1993)), would render the molecule non-immunoreactive. On the other hand partial amino-terminus degradation would result in peptides able to bind to the anti-Met-callatostatin antibodies present in the RIA solution. The mixture remaining after incubation would, therefore, contain all intact molecules and any degradation products with a carboxy-terminus of sufficient length to cross-react within the RIA.

Experiments were carried out in an insect Ringer's solution containing Hepes buffer (Holman et al in *Insect Biochem* 21 107–112 (1991)) at 24° C. and pH 7.0 over several time periods from 15 minutes to 24 hours. In some experiments EDTA (10 mM final concentration) was added with the purpose of inhibiting metalloendopeptidases. For both C. vomitoria and P. americana 1 μl of a 1 μl/μl peptide solution was added to 20 μl of Ringer's solution and 15 μl pooled haemolymph. For C. vomitoria 15 μl was taken from the pooled haemolymph of 10 vitellogenic females, and for P. americana the same volume was obtained from 3–4 ootheca-carrying females. At the conclusion of the incubation period 5 μl of an 8% solution of trichloroacetic acid was added to stop the degradation process. The mixture was centrifuged for 1 minute, an 40 μl of the supernatant was added to 20 μl of water, 0.1% trifluoroacetic acid (TFA) prior to chromatography.

Chromatography was carried out on a Kromasil™ (Technicol) C$_{18}$ 250×4.6 mm, 5 μm, 300 Å column with a gradient of 0–30% CH$_3$CN, 0.1% TFA at a flow rate of 1 ml/min with a rate of change of 1.0%/min. Fractions that were immunoreactive in the Met-callatostatin RIA were rechromatographed on a Delta Pak™ (Waters) C18 250×2.1 mm, 5 μm, 300 Å column with a gradient of 10–30% CH$_3$CN, 0.1% TFA at a flow rate of 0.2 ml/min with a rate of change of 0.5%/min. Peaks of Met-callatostatin-immunoreactive material were measured by RIA, and amino acid sequences were determined.

Degradation of both forms of Met-callatostatin occurred when the peptides were incubated with samples of pooled haemolymph. In C. vomitoria, there was no significant difference in the rates of degradation of the two peptides with approximately 60% remaining after a 2-hour period. When incubated in the haemolypmh of P. americana Met-callatostatin was degraded to approximately the same extent as in C. vomitoria, but [Hyp$^3$]Met-callatostatin was more resistant, as is shown in FIG. 3.

FIG. 3 shows the degradation of Met-callatostatin and [Hyp$^3$]Met-callatostatin (SEQ ID NOS:8 and 2, respectively) as the percentage degradation of 1 μg quantities of Met-callatostatin and [Hyp$^3$]Met-callatostatin incubated with 15 μl of haemolymph of C. vomitoria and P. americana over a 2-hour period at 24° C. in insect Ringer's solution, pH 6.5–7.0. EDTA was added to give 10 mM concentration. The asterisks (*) indicate significant differences in P. americana between Met-callatostatin and [Hyp$^3$] Met-callatostatin (**, p<0.01) and Met-callatostatin and Met-callatostatin plus EDTA (*, p<0.005) (Callatostatin is abbreviated to cast in the figure). Incubation in the presence of EDTA produced a significant reduction in the degradation of the Met-callatostatin in P. americana but not in C. vomitoria, again as is shown in FIG. 3. After 24 hours less than 10% of both peptides remained.

At the end of a 2-hour incubation period it was possible to identify only the reduced and oxidised forms of the parent compounds in C. vomitoria whereas, in P. americana, the carboxy-terminal pentapeptide Tyr-Asp-Phe-Gly-Met-NH$_2$ (SEQ ID NO:9) appeared as a cleavage product of Met-callatostatin, although not of [Hyp$^3$]Met-callatostatin.

It therefore appears that enzymes in the haemolymph of cockroaches are able to degrade Cast-5 (SEQ ID NO:8) (Gly-Pro-Pro-) but not the two peptides with the Gly-Hyp-Pro (SEQ ID NO:1) or Gly-Pro-Hyp (SEQ ID NO:2) motifs. Hydroxylation of the proline residues appears to confer a conformational stability to the molecules which protects them against enzymatic degradation.

Example 10: Immunocytochemical localisation of peptides in C. vomitoria

Immunocytochemical methods

A variety of tissues including brain, corpora cardiaca-CA-hypocerebral ganglion complex, thoracicoabdominal ganglion, and the entire gut were fixed in aqueous Bouin's fluid, embedded in paraffin, and sectioned at 6 μm (Duve et al in *Cell Tissue Res.* 251, 399–415 (1988)). The peroxidase-antiperoxidase method of Sternberger (publ. "*Immunocytochemistry*" 1974)) was used in combination with the three Met-callatostatin antisera, from rabbits D1, D2 and D3, each of which gave essential, the same results. The results presented here were obtained mainly with antiserum from rabbit D1 bleed 5 used at a concentration of 1:2000 for 24 h at 4° C. Other tissues, including the brain, thoracicoabdominal ganglion, and the gut, complete with its neural connections, were fixed in 4% paraformaldehyde for wholemount studies using the indirect immunofluorescence technique with either UV or confocal laser scanning microscopy. After fixation, tissues were washed in phosphate-buffered saline and permeabilized in methanol in phosphate-buffered saline. The tissues were washed in phosphate-buffered saline containing 0.2% bovine serum albumin and Triton X-100 (PBT buffer). Incubation of tissues with the Met-callatostatin antisera was at 4° C. over 24 h. After incubation the tissues were washed in PBT buffer followed by PBT buffer containing 5% swine serum before incubation with swine anti-rabbit fluorescein-isothiocyanate conjugate (1:20) at 4° C. for 24 h (Duve et al in *Cell Tissue Res.* 276, 367–379 (1994)). Finally the tissues were washed in PBT buffer and mounted in 50% glycerol containing 0.1% 1,4-phenylenediamine as an anti-fading reagent. Control experiments for the two types of ICC studies included liquid-phase absorption of antisera with Met-callatostatin (SEQ ID NO:8), [Hyp$^3$]Met-callatostatin (SEQ ID NO:2), and Leu-callatostatins 1 (SEQ ID NO:4) and 3 (SEQ ID NO:6). Whereas both types of Met-callatostatin abolished the immunostaining at 50 μM, Leu-callatostatins, at the same concentration, did not. These results indicate that the antisera are specific for Met-callatostatin. Preliminary ICC studies were carried out on the brain of *C. vomitoria* in an attempt to identify cells that may be engaged in hydroxylation. The antisera used were a polyclonal antiserum recognising the β-subunit of human prolyl 4-hydroxylase (Kivirikko et al in "*Post-translational Modifications of Proteins*", 1–51 ed.s Harding and Crabb (1992)) and two monoclonal antisera, α0-3 and α5-3 raised against the carboxyl and amino termini of the α-subunit of rat prolyl 4-hydroxylase respectively (John et al in *EMBO J.* 12, 1587–1595 (1993)). Approximately 50 vitellogenic females and 20 males were used.

Results

It was not possible to distinguish between the Hyp$^3$ (SEQ ID NO:2) and Pro$^3$ (SEQ ID NO:8) forms of Met-callatostatin by means of ICC, and the following is a description of the neurons within the brian and the abdominal ganglion that are immunoreactive to antisera directed gainst the carboxy-terminus of Met-callatostatin.

Except for a group of three dorsolateral neurosecretory cells and a pair of perikarya located between the roots of the posterior tegumentary nerves, all other Met-callatostatin-immunoreactive cells have been described earlier using antisera to Leu-callatostatin (SEQ ID NOS:4–7) (Duve et al in *Cell Tissue Res.* 276, 367–379 (1994)). Certain cells always appeared strongly immunoreactive. These included a pair of perikarya dorsal to the optic tract and their varicosities in the dorsolateral protecerebrum. Also strongly immunoreactive were a pair of cells between the posterior tegumentary nerves and a pair of perikarya in the subesophageal ganglion in close proximity to the maxillary nerve. The axons of the latter cells project to the thoracic ganglion (Duve et al in *Cell Tissue Res.* 276, 367–379 (1994)). One pair of cells, less intensely immunostained with the Met-callatostatin anti-serum, localised posteriorly in the rind of the tritocerebrum also showed immunoreactivity to the prolyl 4-hydroxylase β subunit antiserum, the only one of the three hydroxylase antisera to give a positive response. In addition to the identified neurons. Met-callatostatin immunoreactivity occurred in certain of the glomeruli of the antennal lobes and the roots of the antennal nerves.

Of the seven neurons in the abdominal ganglion that have been previously identified with Leu-callatostatin antisera (Duve et al in *Cell Tissue Res.* 276, 367–379 (1994)) only the five most dorsally positioned cells showed Met-callatostatin immunoreactivity and often only three of these five cells were visible. The axons of these neurons project posteriorly to the hindgut where intense innervation of the hindgut muscle could be observed. There are also numerous Met-callatostatin immunoreactive endocrine cells in the posterior part of the midgut.

From the evidence of the immunocytochemical studies the peptides also appear to play an important role in neurotransmission and neuromodulation. The appearance of many fibres in the antennal commissure and the glomeruli of the antennal lobes suggest a chemosensory regulatory role.

Example 11: Bioactivity of the peptides in Codling moth larvae

The effect of both the Met- and [Hyp$^3$]Met-callatostatin (SEQ ID NOS:8 and 2, respectively) peptides on the motility of the gut of *C. pomonella* larva were investigated.

The entire gut of the fifth instar larva of the codling moth *Cydia pomonella* was gently pulled through the cuticle. The peristaltic movements of the gut were recorded as visual microscopic observations.

The experimental procedure consisted of an initial superfusion of the preparation with several washes of Ringer, described in Duve et al in *Regul. Pept.* 35, 145–149 (1991), then replacement with fresh Ringer for 1 minute, followed by 2 minute observation, during which time the number of peristaltic movements was counted. The test solution was replaced with fresh Ringer containing the peptide after which the procedure was repeated with variations in concentration of either the same or different peptides. Approximately 50 larvae were used, each preparation remaining stable for up to 3 hours. Peptide solutions were made up in Ringer on the day of the experiments which were carried out at room temperature generally between 21° C. and 25° C.

We have therefore shown that they are active inhibitors of the gut muscle of codling moth larvae, a finding that could possibly be exploited to combat this serious lepidopteran pest of apple orchards world-wide.

We claim:

1. A peptide having the following amino acid sequence: Gly-Xaa-Pro-Tyr-Asp-Phe-Gly-Met-$NH_2$ (SEQ ID NO:1), wherein Xaa is hydroxyproline.

2. A peptide having the following amino acid sequence: Gly-Pro-Xaa-Tyr-Asp-Phe-Gly-Met-$NH_2$ (SEQ ID NO:2), wherein Xaa is hydroxyproline.

3. A peptide consisting of the following amino acid sequence:
Pro-Tyr-Asp-Phe-Gly-Met-$NH_2$ (SEQ ID NO:3).

4. An isolated or purified peptide comprising an amino acid sequence selected from the group consisting of:
Gly-Xaa-Pro-Tyr-Asp-Phe-Gly-Met-$NH_2$ (SEQ ID NO:1) and Gly-Pro-Xaa-Tyr-Asp-Phe-Gly-Met-NH$_2$ (SEQ ID NO:2), wherein Xaa is hydroxyproline, or an isolated purified peptide consisting of Pro-Tyr-Asp-Phe-Gly-Met-NH$_2$ (SEQ ID NO:3).

5. A method for preparing the peptide of claim 4 comprising ligating successive amino acid residues, wherein said ligation is accomplished using synthetic peptide chemistry.

6. A method for preparing the peptide of claim 4 comprising introducing a nucleic acid encoding said peptide and a nucleic acid encoding a prolylhydroxylase enzyme into a host cell under conditions such that said peptide is expressed by the host cell.

7. A method of controlling insects comprising administering to the insects the peptide of any one of claims 1 to 3 or claim 4.

8. An insecticidal formulation comprising a peptide as claimed in claim 4 and a suitable carrier, diluent or excipient therefor.

9. An insecticidal formulation as claimed in claim 8, which is a liposomal formulation.

10. A process for the preparation of an insecticidal composition, comprising admixing a peptide as claimed in any one of claims 1 to 3 or claim 4 with a suitable carrier, diluent or excipient therefor.

11. A method of killing insects comprising administering to the insects an effective amount of an insecticidal formulation as claimed in claim 8.

12. A method of controlling insects comprising administering to the insects an insecticidal formulation as claimed in claim 8.

13. A method as claimed in claim 11 or claim 12, in which the insecticidal formulation is administered in the form of a spray.

14. The method of claim 7, in which the peptide acts as an inhibitor of gut motility.

15. The method of claim 7, in which the peptide is effective against the coddling moth *Cydia pomonella*.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 8 amino acids
        ( B ) TYPE: amino acid (C) STRANDEDNESS: Not Relevant
            (D) TOPOLOGY: linear (ii) MOLECULE TYPE: peptide (vi) ORIGINAL SOURCE:
            (A) ORGANISM: Calliphora vomitoria (ix) FEATURE:
            (A) NAME/KEY: Modified-site
            (B) LOCATION: 2
            (D) OTHER INFORMATION: /note= "Hydroxyproline residue at
        position 2"

(ix) FEATURE:
            (A) NAME/KEY: Modified-site
            (B) LOCATION: 8
            (D) OTHER INFORMATION: /note= "Amidated methionine residue
    at position 8"

(xi) SEQUENCE DESCRIPTION: SEQ ID NO:1:

Gly  Xaa  Pro  Tyr  Asp  Phe  Gly  Met
    1                   5

(2) INFORMATION FOR SEQ ID NO:2:

(i) SEQUENCE CHARACTERISTICS:
            (A) LENGTH: 8 amino acids
            (B) TYPE: amino acid
            (C) STRANDEDNESS: Not Relevant
            (D) TOPOLOGY: linear (ii) MOLECULE TYPE: peptide (vi) ORIGINAL SOURCE:
            (A) ORGANISM: Calliphora vomitoria (ix) FEATURE:
            (A) NAME/KEY: Modified-site
            (B) LOCATION: 3
            (D) OTHER INFORMATION: /note= "Hydroxyproline residue at
        position 3"

(ix) FEATURE:
            (A) NAME/KEY: Modified-site
            (B) LOCATION: 8
            (D) OTHER INFORMATION: /note= "Amidated methionine residue
    at position 8"

(xi) SEQUENCE DESCRIPTION: SEQ ID NO:2:

Gly  Pro  Xaa  Tyr  Asp  Phe  Gly  Met
    1                   5

(2) INFORMATION FOR SEQ ID NO:3:

(i) SEQUENCE CHARACTERISTICS:
            (A) LENGTH: 6 amino acids
            (B) TYPE: amino acid
            (C) STRANDEDNESS: Not Relevant
            (D) TOPOLOGY: linear (ii) MOLECULE TYPE: peptide (vi) ORIGINAL SOURCE:
            (A) ORGANISM: Calliphora vomitoria (ix) FEATURE:
            (A) NAME/KEY: Modified-site
            (B) LOCATION: 6
            (D) OTHER INFORMATION: /note= "Amidated methionine residue
    at position 6"

(xi) SEQUENCE DESCRIPTION: SEQ ID NO:3:

Pro  Tyr  Asp  Phe  Gly  Met
    1                   5

( 2 ) INFORMATION FOR SEQ ID NO:4:

( i ) SEQUENCE CHARACTERISTICS:
        ( A ) LENGTH: 16 amino acids
        ( B ) TYPE: amino acid
        ( C ) STRANDEDNESS: Not Relevant
        ( D ) TOPOLOGY: linear ( i i ) MOLECULE TYPE: peptide ( v i ) ORIGINAL SOURCE:
        ( A ) ORGANISM: Calliphora vomitoria ( i x ) FEATURE:
        ( A ) NAME/KEY: Modified-site
        ( B ) LOCATION: 16
        ( D ) OTHER INFORMATION: /note= "Amidated leucine residue at position 16"

( x i ) SEQUENCE DESCRIPTION: SEQ ID NO:4:

```
Asp  Pro  Leu  Asn  Glu  Glu  Arg  Arg  Ala  Asn  Arg  Tyr  Gly  Phe  Gly  Leu
 1              5                        10                       15
```

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( C ) STRANDEDNESS: Not Relevant
        ( D ) TOPOLOGY: linear ( i i ) MOLECULE TYPE: peptide ( v i ) ORIGINAL SOURCE:
        ( A ) ORGANISM: Calliphora vomitoria ( i x ) FEATURE:
        ( A ) NAME/KEY: Modified-site
        ( B ) LOCATION: 14
        ( D ) OTHER INFORMATION: /note= "Amidated leucine residue at position 14"

( x i ) SEQUENCE DESCRIPTION: SEQ ID NO:5:

```
Leu  Asn  Glu  Glu  Arg  Arg  Ala  Asn  Arg  Tyr  Gly  Phe  Gly  Leu
 1              5                        10
```

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: peptide ( v i ) ORIGINAL SOURCE:
        ( A ) ORGANISM: Calliphora vomitoria ( i x ) FEATURE:
        ( A ) NAME/KEY: Modified-site
        ( B ) LOCATION: 8
        ( D ) OTHER INFORMATION: /note= "Amidated leucine at position 8"

( x i ) SEQUENCE DESCRIPTION: SEQ ID NO:6:

```
Ala  Asn  Arg  Thr  Gly  Phe  Gly  Leu
 1              5
```

( 2 ) INFORMATION FOR SEQ ID NO:7:

( i ) SEQUENCE CHARACTERISTICS:

-continued

```
        (A) LENGTH: 8 amino acids
        (B) TYPE: amino acid
        (C) STRANDEDNESS: Not Relevant
        (D) TOPOLOGY: linear (i i) MOLECULE TYPE: peptide (v i) ORIGINAL SOURCE:
        (A) ORGANISM: Calliphora vomitoria (i x) FEATURE:
        (A) NAME/KEY: Modified-site
        (B) LOCATION: 8
        (D) OTHER INFORMATION: /note= "Amidated leucine residue at
position 8"

(x i) SEQUENCE DESCRIPTION: SEQ ID NO:7:

Asx  Arg  Pro  Tyr  Ser  Phe  Gly  Leu
    1                   5

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: Not Relevant
        (D) TOPOLOGY: linear (i i) MOLECULE TYPE: peptide (v i) ORIGINAL SOURCE:
        (A) ORGANISM: Calliphora vomitoria (i x) FEATURE:
        (A) NAME/KEY: Modified-site
        (B) LOCATION: 8
        (D) OTHER INFORMATION: /note= "Amidated methionine residue
at position 8"

(x i) SEQUENCE DESCRIPTION: SEQ ID NO:8:

Gly  Pro  Pro  Tyr  Asp  Phe  Gly  Met
    1                   5

(2) INFORMATION FOR SEQ ID NO:9:

(i) SEQUENCE CHARACTERISTICS:
        (A) LENGTH: 5 amino acids
        (B) TYPE: amino acid
        (C) STRANDEDNESS: Not Relevant
        (D) TOPOLOGY: linear (i i) MOLECULE TYPE: peptide (v i) ORIGINAL SOURCE:
        (A) ORGANISM: Calliphora vomitoria (i x) FEATURE:
        (A) NAME/KEY: Modified-site
        (B) LOCATION: 5
        (D) OTHER INFORMATION: /note= "Amidated methionine residue
at position 5"

(x i) SEQUENCE DESCRIPTION: SEQ ID NO:9:

Tyr  Asp  Phe  Gly  Met
    1                   5
```